United States Patent [19]

Schirmer et al.

[11] 4,396,418
[45] Aug. 2, 1983

[54] N-ARYL(THIO)CARBAMATES, THE MANUFACTURE THEREOF, AND THE USE THEREOF FOR COMBATING UNWANTED PLANT GROWTH

[75] Inventors: Ulrich Schirmer, Heidelberg; Rainer Becker, Bad Durkheim; Bruno Wuerzer, Otterstadt; Guenter Retzlaff, Roemerberg, all of Fed. Rep. of Germany

[73] Assignee: BASF Aktiengesellschaft, Fed. Rep. of Germany

[21] Appl. No.: 259,543

[22] Filed: May 1, 1981

Related U.S. Application Data

[63] Continuation-in-part of Ser. No. 236,921, Feb. 23, 1981, abandoned.

[30] Foreign Application Priority Data

Mar. 8, 1980 [DE] Fed. Rep. of Germany ....... 3008985

[51] Int. Cl.³ ................. C07C 155/02; C07C 125/06; A01N 31/14; A01N 37/44
[52] U.S. Cl. .................... 71/98; 260/455 A; 560/27; 71/100; 71/103; 71/111
[58] Field of Search ............. 260/455 A; 560/27; 71/100, 98, 103, 111

[56] References Cited

U.S. PATENT DOCUMENTS 3,971,649  7/1976  Baker ............................... 260/455 A
3,976,470  8/1976  Baker ............................... 260/455 A Primary Examiner—John M. Ford
Assistant Examiner—Robert C. Whittenbaugh
Attorney, Agent, or Firm—Keil & Witherspoon

[57] ABSTRACT

N-aryl(thiol)carbamates of the formula

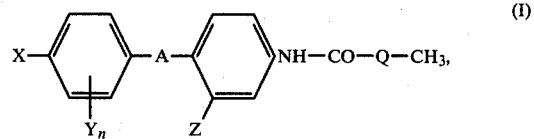

where X denotes hydrogen, fluorine, bromine, iodine, alkyl, alkoxy, haloalkyl, haloalkoxy, alkylthio, alkylsulfinyl or alkylsulfonyl of 1 to 6 carbon atoms, cycloalkyl of 3 to 6 carbon atoms, phenyl or benzyloxy, Y denotes hydrogen, halogen, alkyl, alkoxy, haloalkyl, haloalkoxy, alkylthio, alkylsulfinyl or alkylsulfonyl of 1 to 6 carbon atoms, cycloalkyl of 3 to 6 carbon atoms, phenyl or benzyloxy, n denotes one of the integers 1 and 2, Z denotes hydrogen, halogen or trifluoromethyl, A denotes oxygen, sulfur, sulfinyl or sulfonyl, and Q denotes oxygen or sulfur, and their use for combating unwanted plant growth.

10 Claims, No Drawings

N-ARYL(THIOL)CARBAMATES, THE MANUFACTURE THEREOF, AND THE USE THEREOF FOR COMBATING UNWANTED PLANT GROWTH

This application is a continuation-in-part application of Serial No. 236,921, filed Feb. 23, 1981, now abandoned.

The present invention relates to N-aryl(thiol)-carbamates, a process for their manufacture, herbicides containing these compounds as active ingredients, and a process for combating unwanted plant growth with these compounds.

The herbicidal effectiveness of S-methyl-N-[4-(4'-chlorophenoxy)-phenyl]-thiolcarbamate (U.S. Pat. No. 3,971,649) and S-methyl-N-[4-(4'-chlorophenoxy)-3-chlorophenyl]-thiolcarbamate (U.S. Pat. No. 3,976,470) has been disclosed.

We have found that N-aryl(thiol)carbamates of the formula

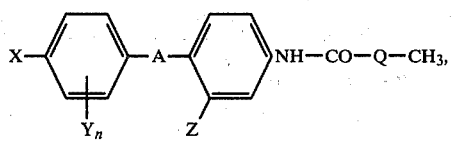

(I)

where X denotes hydrogen, fluorine, bromine, iodine, alkyl, alkoxy, haloalkyl, haloalkoxy, alkylthio, alkylsulfinyl or alkylsulfonyl of 1 to 6 carbon atoms, cycloalkyl of 3 to 6 carbon atoms, phenyl or benzyloxy, Y denotes hydrogen, halogen, alkyl, alkoxy, haloalkyl, haloalkoxy, alkylthio, alkylsulfinyl or alkylsulfonyl of 1 to 6 carbon atoms, cycloalkyl of 3 to 6 carbon atoms, phenyl or benzyloxy, n denotes one of the integers 1 and 2, Z denotes hydrogen, halogen or trifluoromethyl, A denotes oxygen, sulfur, sulfinyl or sulfonyl, and Q denotes oxygen or sulfur, have an unexpectedly good herbicidal action on a number of broadleaved unwanted plants. The herbicidal action is superior to that of prior art N-aryl(thiol)-carbamates, and the compounds according to the invention are exceedingly well tolerated by crops from the Gramineae family and—especially—by broadleaved crop plants.

In formula I, X and Y denote hydrogen, phenyl or benzyloxy, halogen, such as fluorine, bromine and iodine (Y may also denote chlorine), X and Y may further denote linear or branched alkyl, alkoxy, haloalkyl, haloalkoxy, alkylthio, alkylsulfinyl or alkylsulfonyl of from 1 to 6 carbon atoms, preferably from 1 to 4 carbon atoms, or cycloalkyl of from 3 to 6 carbon atoms, such as methyl, ethyl, isopropyl, n-propyl, isobutyl, tert-butyl, n-pentyl, n-hexyl, methoxy, ethoxy, isopropoxy, n-propoxy, sec-butoxy, trifluoromethyl, difluoromethoxy, trifluoromethoxy, 2-chloro-2,1,1-trifluoroethoxy, methylthio, methylsulfonyl, isopropylthio and cyclohexyl.

Z in formula I denotes hydrogen, halogen, such as fluorine, chlorine and bromine, or trifluoromethyl, Preferred compounds of the formula I are those in which X is hydrogen or alkyl, alkoxy or haloalkoxy of from 1 to 4 carbon atoms.

The N-aryl(thiol)carbamates of the formula I are obtained by reaction of amines of the formula

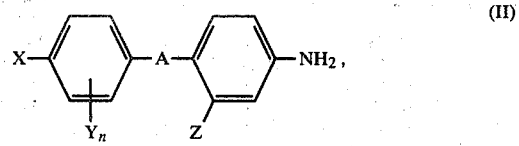

(II)

where X, Y, Z, A and n have the above meanings, with the chloroformic acid (thio)methyl ester of the formula $$Cl-CO-Q-CH_3 \quad (III),$$

where Q has the above meanings, in the presence of an acid-binding agent and a solvent.

Examples of suitable solvents are water; alcohols, especially aliphatic alcohols, such as methanol, ethanol and isopropanol; chlorinated aliphatic hydrocarbons, such as chloroform, methylene chloride and dichloroethane; and ketones, such as acetone, diethyl ketone and methyl ethyl ketone.

Suitable acid binders are the bases conventionally used, such as alkali metal hydroxides, bicarbonates and carbonates, alkaline earth metal oxides, hydroxides, bicarbonates and carbonates, and tertiary organic bases. Sodium hydroxide, sodium carbonate, sodium bicarbonate, calcium oxide, triethylamine, pyridine, N,N-dimethylaniline, N,N-dimethylcyclohexylamine, quinoline and tri-n-butylamine are particularly suitable.

The starting materials of the formulae II and III are reacted in an approximately stoichiometric ratio, i.e., from 0.9 to 1.1 moles of the starting material of the formula II is advantageously used per mole of starting compound of the formula III. The reaction is carried out at from $-20°$ to $+150°$ C., preferably from $+20°$ to $60°$ C.

Some of the amines of the formula II are known; they may be prepared by the methods described in Houben-Weyl, Methoden der organ. Chemie, XI/1, 341 et seq., Georg Thieme-Verlag, Stuttgart, 1957.

EXAMPLE

A solution of 12.6 parts by weight of sodium bicarbonate in 200 parts by weight of water is added to 25.0 parts by weight of 4-(4'-methoxyphenoxy)-3-chloroaniline which has been dissolved in 200 parts by weight of acetone. Subsequently, 9.45 parts by weight of methyl chloroformate is added and, after the mixture has been stirred for a few hours at room temperature, it is introduced into water; the organic phase is extracted with methylene chloride and concentrated. The oil which remains crystallizes with cyclohexane. There is obtained 28.2 parts of N-[4-(4'-methoxyphenoxy)-3-chlorophenyl]-carbamic acid methyl ester of melting point $95°-98°$ C.

The following compounds, for instance, may be prepared analogously:

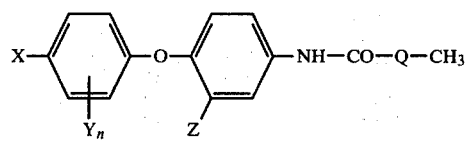

| No. | X | $Y_n$ | Z | Q | M.p. [°C.] |
|---|---|---|---|---|---|
| 1 | CH$_3$O | H | Cl | O | 95-98 |
| 2 | i-C$_3$H$_7$O | H | Cl | O | 66-68 |

-continued

| No. | | | | | M.p. [°C.] |
|---|---|---|---|---|---|
| 3 | CH₃ | H | Cl | O | 89-91 |
| 4 | CH₃O | H | CF₃ | O | 108-111 |
| 5 | H | 3-CH₃O | Cl | O | 60-63 |
| 6 | i-C₃H₇O | H | Cl | S | 85-88 |
| 7 | n-C₃H₇O | H | Cl | S | 68-70 |
| 8 | F | H | Cl | O | |
| 9 | Br | H | Cl | O | 108-110 |
| 10 | H | H | H | O | 90-92 |
| 11 | H | H | CF₃ | S | |
| 12 | CF₃ | H | H | O | |
| 13 | CF₃ | H | Br | O | |
| 14 | n-C₃H₇ | H | Cl | S | |
| 15 | i-C₃H₇ | H | Cl | S | 106-109 |
| 16 | H | 3-CH₃O | Cl | S | 123-125 |
| 17 | CH₃ | 2-Cl | Cl | O | |
| 18 | F | H | Cl | S | |
| 19 | i-C₃H₇ | H | Br | O | |
| 20 | i-C₃H₇O | H | CF₃ | O | |
| 21 | CF₃ | H | H | S | |
| 22 | CH₃O | H | H | S | 122-124 |
| 23 | CH₃O | H | H | O | 88-91 |
| 24 | H | 2-Cl | Cl | S | 104-106 |
| 25 | FClCH—CF₂O | H | Cl | S | 81-83 |
| 26 | CF₃O | H | Cl | S | 120-122 |
| 27 | CH₃O | H | CF₃ | S | oil |
| 28 | CH₃O | H | Br | S | 119-121 |
| 29 | C₂H₅O | H | Cl | O | 99-102 |
| 30 | n-C₃H₇O | H | Cl | O | 48-52 |
| 31 | CHF₂O | H | Cl | O | 68-70 |
| 32 | n-C₃H₇ | H | Cl | O | oil |
| 33 | i-C₃H₇ | H | Cl | O | 69-71 |
| 34 | CH₃O | H | F | O | 85-87 |
| 35 | CH₃O | H | Br | O | 98-100 |
| 36 | CF₃ | H | Br | O | |
| 37 | H | 3-Cl | Cl | O | 46-49 |
| 38 | CH₃ | 2-CH₃ | Cl | O | |
| 39 | CH₃O | H | Cl | S | 104-106 |
| 40 | C₂H₅O | H | Cl | S | 101-104 |
| 41 | i-C₃H₇ | H | H | O | |
| 42 | i-C₃H₇O | H | H | O | |
| 43 | H | H | H | S | 91-93 |
| 44 | i-C₃H₇O | H | F | S | |
| 45 | i-C₃H₇ | H | Br | S | |
| 46 | CHF₂O | H | H | O | 77-78 |
| 47 | FClCH—CF₂O | H | H | S | 109-111 |
| 48 | i-C₃H₇O | H | H | S | |
| 49 | H | H | CF₃ | O | |
| 50 | i-C₃H₇O | H | Br | S | |
| 51 | FClCH—CF₂O | H | Cl | O | 62-65 |
| 52 | CF₃O | H | Cl | O | |
| 53 | H | 3-CHF₂O | Cl | O | |
| 54 | CF₃ | H | Cl | O | 104-107 |
| 55 | i-C₃H₇O | H | Br | O | |
| 56 | i-C₃H₇ | H | CF₃ | O | |
| 57 | H | 2-Cl | Cl | O | |
| 58 | i-C₃H₇ | 2-Cl | Cl | O | |
| 59 | CHF₂O | H | Cl | S | 93-95 |
| 60 | H | 3-CHF₂O | Cl | S | |
| 61 | Br | H | Cl | S | 150-152 |
| 62 | CH₃ | H | Cl | S | 124-127 |
| 63 | CH₃O | H | F | S | 91-93 |
| 64 | FClCH—CF₂O | H | H | O | 77-79 |
| 65 | i-C₃H₇ | H | F | S | |
| 66 | CF₃ | H | F | S | |
| 67 | H | H | Cl | S | 116-118 |
| 68 | CHF₂O | H | H | S | 82-84 |
| 69 | i-C₃H₇ | H | H | S | |
| 70 | H | H | Cl | O | 108-110 |
| 71 | H | 3-Cl | Cl | S | |
| 72 | CH₃ | 2-Cl | Cl | S | |
| 73 | CF₃ | H | Cl | S | 120-122 |
| 74 | CH₃O | 2-Cl | Cl | S | |
| 75 | CH₃O | 3-Cl | Cl | O | |
| 76 | CH₃O | 2-Cl | Cl | S | |
| 77 | H | 2-Cl, 5-OCH₃ | Cl | S | |
| 78 | CF₃ | 2-Cl | Cl | O | |
| 79 | CH₃O | 3-Cl | Cl | S | |
| 80 | CF₃ | 2-Cl | Cl | S | |
| 81 | H | 2-Cl, 5-OCH₃ | Cl | O | |
| 82 | tert-C₄H₉ | H | Cl | O | 96-98 |
| 83 | CH₃S | H | Cl | O | 79-80 |
| 84 | tert-C₄H₉ | H | Cl | S | 90-92 |
| 85 | C₆H₅CH₂O | H | Cl | O | 131-133 |
| 86 | CH₃S | H | Cl | S | 137-139 |
| 87 | C₆H₅ | H | Cl | S | 120-122 |
| 88 | C₆H₅CH₂O | H | Cl | S | 123-125 |
| 89 | C₆H₁₁ | H | Cl | S | 115-118 |
| 90 | C₆H₁₁ | H | Cl | O | 114-116 |
| 91 | C₆H₅ | H | Cl | O | 131-133 |
| 92 | i-C₄H₉ | H | Cl | S | oil |
| 93 | i-C₄H₉ | H | Cl | O | oil |
| 94 | CH₃SO₂ | H | Cl | S | |
| 95 | CH₃SO₂ | H | Cl | O | 154-156 |
| 96 | H | 3-CH₃ | Cl | O | 59-63 |
| 97 | H | 3-CH₃ | Cl | S | |
| 98 | C₂H₅ | H | Cl | O | 130-133 |
| 99 | C₂H₅ | H | Cl | S | 73-74 |
| 100 | OCF₂CHFCF₃ | H | Cl | O | 63-67 |
| 101 | H | 2-OCH₃ | Cl | O | 90-93 |
| 102 | CH₃ | 3-CH₃ | Cl | O | 79-81 |
| 103 | tert-C₅H₁₁ | H | Cl | O | 84-86 |
| 104 | i-C₃H₇ | 2-CH₃ | Cl | O | oil |
| 105 | CH₂—C₆H₅ | H | Cl | O | 105-107 |
| 106 | i-C₃H₇ | 2-CH₃ | Cl | S | |
| 107 | C₆H₅ | H | Cl | S | 123-125 |
| 108 | C₆H₅ | H | Cl | O | 131-133 |

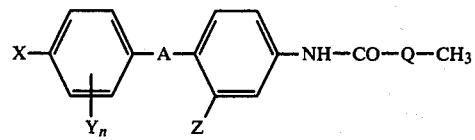

$$X \!-\!\!\!\bigcirc\!\!\!-\!A\!-\!\!\!\bigcirc\!\!\!-\!NH\!-\!CO\!-\!Q\!-\!CH_3$$

| No. | X | Yₙ | Z | Q | A | M.p. [°C.] |
|---|---|---|---|---|---|---|
| 109 | CH₃O | H | Cl | O | S | 99-102 |
| 110 | CH₃O | H | Cl | S | S | 120-122 |
| 111 | tert-C₄H₉ | H | Cl | O | S | 113-115 |
| 112 | CH₃ | H | Cl | S | S | 137-139 |
| 113 | CHF₂O | H | Cl | S | S | 77-78 |
| 114 | tert-C₄H₉ | H | Cl | S | S | 134-137 |
| 115 | CH₃O | H | Cl | S | SO₂ | |
| 116 | CH₃O | H | Cl | O | SO₂ | 180-183 |
| 117 | CHF₂O | H | Cl | O | S | 63-65 |
| 118 | CH₃ | H | Cl | O | S | 100-103 |
| 119 | tert-C₄H₉ | H | Cl | O | SO₂ | |
| 120 | tert-C₄H₉ | H | Cl | S | SO₂ | |
| 121 | CHF₂O | H | Cl | S | SO₂ | |
| 122 | CHF₂O | H | Cl | O | SO₂ | |
| 123 | H | H | Cl | S | S | 141-143 |
| 124 | H | H | Cl | O | S | |
| 125 | i-C₃H₇O | H | Cl | O | S | 83-85 |
| 126 | i-C₃H₇O | H | Cl | S | S | 72-73 |
| 127 | H | 2-Cl, 5-Cl | Cl | S | S | 117-119 |
| 128 | H | 2-Cl, 5-Cl | Cl | O | S | 105-108 |
| 129 | H | H | H | S | S | |
| 130 | C₆H₅ | H | H | O | O | 178-180 |
| 131 | C₆H₅ | H | H | S | O | 178-180 |
| 132 | sec-C₄H₉ | H | Cl | O | O | oil |
| 133 | sec-C₄H₉ | H | Cl | S | O | oil |
| 134 | I | H | Cl | O | O | 98-100 |
| 135 | I | H | Cl | S | O | 165-168 |
| 136 | CHF₂O | H | CF₃ | O | O | oil |
| 137 | CHF₂O | H | CF₃ | S | O | 70-73 |
| 138 | CH₃ | 3-CH₃ | Cl | O | O | 79-81 |

The active ingredients according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol, polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

I. 90 parts by weight of compound 1 is mixed with 10 parts by weight of N-methyl-α-pyrrolidone. A mixture is obtained which is suitable for application in the form of very fine drops.

II. 20 parts by weight of compound 43 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound 7 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound 31 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound 40 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 51 is intimately mixed with 97 parts by weight of particulate kaolin. A dust is obtained containing 3% by weight of the active ingredient.

VII. 30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents according to the invention may be applied pre- or postemergence, i.e., before unwanted plants have germinated from seed or sprouted from vegetative plant parts, or to the leaves of unwanted and crop plants. Preferably, the new active ingredients are applied after emergence of the unwanted plants, both to cropland and uncropped land.

If the crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

Depending on the season and the growth stage of the plants, the application rates of active ingredient are from 0.1 to 15 kg/ha and more, the higher rates being particularly suitable for the total elimination of vegetation. Application rates are preferably from 0.5 to 5, and particularly from 0.5 to 2, kg/ha.

The influence of various representatives of N-aryl(-thiol)-carbamates according to the invention on the growth of unwanted plants is demonstrated in greenhouse experiments, in which prior art compounds were used for comparison purposes.

The vessels employed were plastic flowerpots having a volume of 300 cm$^3$, and which were filled with a sandy loam containing about 1.5% humus. The seeds of the test plants were sown shallow, and separately, according to species, or pregerminated young plants were used.

Generally, the plants were grown to a height of 3 to 10 cm, depending on the growth shape, before being treated. The compounds were emulsified or suspended in water as vehicle, and sprayed through finely distributing nozzles onto the shoot parts of the plants and the soil not completely covered by plants. The pots were set up in the greenhouse—species from warmer areas at from 20° to 30° C., and species from moderate climates at 10° to 20° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

For the preemergence treatment in the greenhouse, the same vessels and the same soil were used as for the postemergence treatment. The active ingredients were applied to the surface of the soil immediately after sowing, at a rate of 3.0 kg/ha as a suspension or emulsion in water, by spraying through finely distributing nozzles.

After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals. The scale employed for assessment was the same as for postemergence treatment.

The plants tested were *Abutilon theophrastii* (velvet leaf), *Amaranthus retroflexus* (pigweed), *Arachis Hypogaea* (peanut), *Avena sativa* (oats), *Cassia* spp. (sickle pod), *Chenopodium album* (lambs-quarters), *Centaurea cyanus* (cornflower), *Euphorbia geniculata* (South American member of the spurge family), *Glycine max* (soybeans), *Gossypium hirsutum* (cotton), *Ipomoea* spp. (morningglory), *Lamium* spp. (dead-nettle), *Mercurialis annua* (annual mercury), *Sesbania exaltata* (coffeeweed), *Sida spinosa* (prickly sida), *Sinapis alba* (white mustard), *Stellaria media* (chickweed), *Triticum aestivum* (wheat).

The prior art active ingredients used for comparison purposes were N-[4-(4'chlorophenoxy)-phenyl]-thiolcarbamic acid methyl ester (V$_1$; U.S. Pat. No. 3,971,649) and N-[4-(4'-chlorophenoxy)-3-chlorophenyl]-thiolcarbamic acid methyl ester (V$_2$; U.S. Pat. No. 3,976,470).

I. On postemergence application in the greenhouse, compounds nos. 1, 6, 15, 43, 63, 67 and 70 have, at rates of from 1 to 2 kg/ha, a better herbicidal action in cereals than comparative agent V$_1$.

II. On postemergence treatment in the greenhouse, compounds nos. 2, 7, 25, 47, 51 and 68 have, at application rates of from 0.5 to 1.0 kg/ha, a better herbicidal action than comparative agent V$_2$, and are better tolerated by crop plants.

III. On postemergence application in the greenhouse, compounds nos. 1, 6, 15, 24, 31, 33, 34, 40, 62, 68 and 70 have, at rates of from 0.5 to 1.0 kg/ha, a better action on broadleaved unwanted plants than comparative agent V$_2$.

IV. On postemergence application in the greenhouse, compounds nos. 1, 2, 7, 8, 15, 31, 33, 39, 46 and 84 show, at rates of from 0.5 to 2.0 kg/ha, an excellent herbicidal action on unwanted plants in cereals.

V. On postemergence application in the greenhouse, compounds nos. 10, 16, 22, 29, 59, 61, 64, 85, 88, 89, 90, 91, 98, 99, 100, 109, 110, 111, 112, 114, 117, 118, 123, 125 and 126 have, at a rate of 3.0 kg/ha, an excellent herbicidal action on unwanted plants in cereals.

VI. On preemergence application in the greenhouse, compounds nos. 2, 9, 10, 33, 37, 70, 82 and 84 have, at a rate of 3.0 kg/ha, an excellent action on unwanted plants in cereals.

In view of the good tolerance of the active ingredients, the agents according to the invention, or mixtures containing them, may be used in a wide range of crops for removing unwanted plants.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape seed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |

| Botanical name | Common name |
| --- | --- |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrents |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. inguiculata) | cow peas |
| Vitis vinifera | grapes |
| Zea mays | Indian corn, sweet corn, maize |

To increase the spectrum of action and to achieve synergistic effects, the N-aryl(thiol)carbamates of the formula I may be mixed among themselves and with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenyl-carbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2$\underline{H}$)-pyridazinone
5-amino-4-bromo-2-phenyl-3(2$\underline{H}$)-pyridazinone
5-amino-4-chloro-2-cyclohexyl-3(2$\underline{H}$)-pyridazinone
5-amino-4-bromo-2-cyclohexyl-3(2$\underline{H}$)-pyridazinone
5-methylamino-4-chloro-2-(3-trifluoromethylphenyl)-3(2$\underline{H}$)-pyridazinone
5-methylamino-4-chloro-2-(3-$\alpha,\alpha,\beta,\beta$-tetrafluoroethoxyphenyl)-3(2$\underline{H}$)-pyridazinone
5-dimethylamino-4-chloro-2-phenyl-3(2$\underline{H}$)-pyridazinone
4,5-dimethoxy-2-phenyl-3(2$\underline{H}$)-pyridazinone
4,5-dimethoxy-2-cyclohexyl-3(2$\underline{H}$)-pyridazinone
4,5-dimethoxy-2-(3-trifluoromethylphenyl)-3(2$\underline{H}$)-pyridazinone
5-methoxy-4-chloro-2-(3-trifluoromethylphenyl)-3(2$\underline{H}$)-pyridazinone
5-amino-4-bromo-2-(3-methylphenyl)-3(2$\underline{H}$)-pyridazinone
4,5-dimethoxy-2-(3-$\alpha,\alpha,\beta$-trifluoro-$\beta$-bromoethoxyphenyl)-3(2H)-pyridazinone
3-(1-methylethyl)-1H-2,1,3-benzothiadiazin-4(3$\underline{H}$)-one-2,2-dioxide and salts
3-(1-methylethyl)-8-chloro-1H-2,1,3-benzothiadiazin-4(3$\underline{H}$)-one-2,2-dioxide and salts
3-(1-methylethyl)-8-fluoro-1H-2,1,3- benzothiadiazin-4(3$\underline{H}$)-one-2,2-dioxide and salts
3-(1-methylethyl)-8-methyl-1H-2,1,3-benzothiadiazin-4(3$\underline{H}$)-one-2,2-dioxide and salts
1-methoxymethyl-3-(1-methylethyl)-2,1,3-benzothiadiazin-4(3$\underline{H}$)-one-2,2-dioxide
1-methoxymethyl-8-chloro-3-(1-methylethyl)-2,1,3-benzothiadiazin-4(3$\underline{H}$)-one-2,2-dioxide
1-methoxymethyl-8-fluoro-3-(1-methylethyl)-2,1,3-benzothiadiazin-4(3$\underline{H}$)-one-2,2-dioxide
1-cyano-8-chloro-3-(1-methylethyl)-2,1,3-benzothiadiazin-4(3$\underline{H}$)-one-2,2-dioxide
1-cyano-8-fluoro-3-(1-methylethyl)-2,1,3-benzothiadiazin-4(3$\underline{H}$)-one-2,2-dioxide
1-cyano-8-methyl-3-(1-methylethyl)-2,1,3-benzothiadiazin-4(3$\underline{H}$)-one-2,2-dioxide
1-cyano-3-(1-methylethyl)-2,1,3-benzothiadiazin-4(3$\underline{H}$)-one-2,2-dioxide
1-azidomethyl-3-(1-methylethyl)-2,1,3-benzothiadiazin-4(3$\underline{H}$)-one-2,2-dioxide
3-(1-methylethyl)-1H-pyridino[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-$\beta$-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-($\beta$-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate methyl-N-(3(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate
methyl N-3-(4'-fluorophenoxycarbonylamino)-phenyl-thiolcarbamate
methyl N-3-(2', 4', 5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
ethyl 4-(4'-trifluoromethylphenoxy)-pentene-2-carboxylate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide 2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
N-benzyl-N-isopropyl-trimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyl-trifluoromethanesulfone anilide
5-acetamido-4-methyl-trifluoromethanesulfone anilide
N-4-methyl-5-(trifluoromethyl)-sulfonylamino-phenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneimide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2-chloro-4-trifluoromethylphenyl-3'-ethoxycarbonyl-4'-nitrophenyl ether
2-chloro-4-trifluoromethylphenyl-3'-(2-fluoroethoxy)-4'-nitrophenyl ether
2-chloro-4-trifluoromethylphenyl-3'-ethoxycarbonylmethylthio-4'-nitrophenyl ether
2-chloro-4-trifluoromethyl-3'-methoxycarbonyl-4'-nitrophenyl ether
2,4,6-trichlorophenyl-3-ethoxycarbonyl-methylthio-4'-nitrophenyl ether
2,4-dichlorophenyl-3'-methoxycarbonyl-4'-nitro-phenyl ether
2,4-dichlorophenyl-3'-carboxy-4'-nitrophenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-B 4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4 -methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3dimethylurea
1-(4-fluorophenyl)-3-carboxymethoxy-3-methylurea
1-phenyl-3-methyl-3-methoxyurea
1-(4-chlorophenyl)-3-methyl-3-methoxyurea 1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
1-(4-benzyloxyphenyl)-3-methyl-3-methoxyurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
1-acetyl-3-anilino-4-methoxycarbonyl-5-methyl-pyrazole
3-anilino-4-methoxycarbonyl-5-methyl-pyrazole
3-tert-butylamino-4-methoxycarbonyl-5-methyl-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[2-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5,-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-(2-methylphenoxy)-propionic acid (salts esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides) methyl 2-[4-(4'-chlorophenoxymethyl)-phenoxy]-propionate
4-(2,4-dichlorophenoxy)-butyric acid (salts, esters, amides)
4-(2-methyl-4-chlorophenoxy)-butyric acid (salts, esters, amides) cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
2-[1-(N-ethoxamino)-butylidene]-5-(2-ethylthiopropyl)-3-hydroxycyclohex-2-en-1one (salts)
2-[1-(N-ethoxamino)-butylidene]-5-(2-phenylthiopropyl)-3-hydroxycyclohex-2-en-1-one (salts)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
2-[1-(2,5-dimethylphenyl)-ethylsulfonyl]-pyridine-N-oxide
sodium chlorate
ammonium thiocyanate
calcium cyanamide.

It may also be useful to apply the mixtures according to the invention in admixture with other crop protection agents, e.g., agents for combating pests or phytopathogenic fungi or bacteria. The compounds may also be mixed with solutions of mineral matters used to remedy nutritional or trace element deficiencies. To initiate the herbicidal action, wetting agents, spreader-stickers and non-phytotoxic oils and oil concentrates may be added.

We claim:

1. An N-aryl(thiol)carbamate of the formula

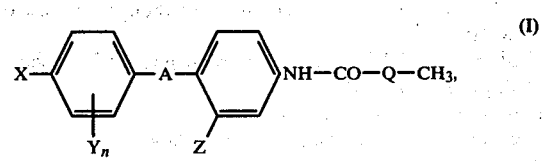

where X denotes hydrogen, fluorine, bromine, iodine, alkyl, alkoxy, haloalkyl, haloalkoxy, alkylthio, alkylsulfinyl or alkylsulfonyl of 1 to 6 carbon atoms, cycloalkyl of 3 to 6 carbon atoms, phenyl or benzyloxy, Y denotes hydrogen, halogen, alkyl, alkoxy, haloalkyl, haloalkoxy, alkylthio, alkylsulfinyl or alkylsulfonyl of 1 to 6 atoms, cycloalkyl of 3 to 6 carbon atoms, phenyl or benzyloxy, n denotes one of the integers 1 and 2, Z denotes hydrogen, halogen, or trifluoromethyl, A denotes oxygen, sulfur, sulfinyl or sulfonyl, and Q denotes oxygen or sulfur.

2. An N-aryl(thiol)carbamate of the formula I as claimed in claim 1, wherein X denotes hydrogen or alkyl, alkoxy or haloalkoxy of from 1 to 4 carbon atoms.

3. N-[4-(4'-methoxyphenoxy)-3-chlorophenyl]-carbamic acid methyl ester.

4. N-[4-(4'-isopropylphenoxy)-3-chlorophenyl]-thiolcarbamic acid methyl ester.

5. A process for combating the growth of unwanted plants, wherein the plants or the soil are treated with a herbicidally effective amount of an N-aryl(thiol)carbamate of the formula I as claimed in claim 1.

6. A compound of the formula (I) as described in claim 1 wherein x denotes hydrogen, alkyl, alkoxy, haloalkyl, haloalkoxy, alkylthio, alkylsulfinyl or alkylsulfonyl of 1 to 6 carbon atoms, cycloalkyl of 3 to 6 carbon atoms, phenyl or benzyloxy.

7. A compound of the formula (I) as defined in claim 1 wherein x is an alkoxy group of 1 to 3 carbon atoms.

8. A compound of the formula (I) as defined in claim 1 wherein x is an alkyl of 1 to 3 carbon atoms.

9. A compound of the formula (I) as defined in claim 1 wherein x is $OCF_2H$.

10. A compound of the formula (I) as defined in claim 1 wherein x is $OCF_2CHFCL$.

* * * * *